United States Patent [19]
Lin et al.

[11] Patent Number: 6,140,503
[45] Date of Patent: Oct. 31, 2000

[54] ORGANOMETALLIC COMPOUNDS

[75] Inventors: Jiann T'suen Lin; Iuan-Yuan Wu, both of Taipei, Taiwan; K. R. Justin Thomas, Vellalanvlai, India

[73] Assignee: Academia Sinica, Taipei, Taiwan

[21] Appl. No.: 09/236,683

[22] Filed: Jan. 25, 1999

[51] Int. Cl.⁷ ...................... C07D 213/04; C07D 207/00; C07D 409/00; C07D 307/02

[52] U.S. Cl. ........................ 546/255; 548/518; 549/59; 549/479

[58] Field of Search ............................ 546/255; 549/479, 549/59; 548/518

[56] References Cited

U.S. PATENT DOCUMENTS

| | | | |
|---|---|---|---|
| 5,334,333 | 8/1994 | Goetz | 252/582 |
| 5,453,522 | 9/1995 | Davis et al. | 552/114 |

OTHER PUBLICATIONS

Bildstein et al., Cationic and Neutral [4]–Cumulenes C=C=C=C=C with Five Cumulated Carbons and Three to Four Ferrocenyl Termini, Organometallics 1998, 17, 2414–2424.

Chen et al., "Synthesis and Linear Optical Sepctroscopy of Thioflavylium Near–Infrared Absorbing Dyes", Adv. Mater. 1995, 7, No. 12, 1030–1033.

Heck et al., "Bimetallic Sandwich–Like Complexes as Novel NLO–Chromophores", SPIE, 1997, vol. 3147, 53–61.

Lee et al., "Dinuclear Complexes Containing Ferrocenyl and Oxomolybdenum (V) Groups Linked by Conjugated Bridges: A new Class of Electrochromic . . . ", Chem. Mater. 1998, 10, 3272–3274.

Tolbert et al., "Bis(ferrocenyl)polymethine Cations. A Prototype Molecular Wire with Redox–Active End Groups", J. Am. Chem. Soc., 1995, 117, 12891–12892.

*Primary Examiner*—Deborah C. Lambkin
*Attorney, Agent, or Firm*—Fish & Richardson P.C.

[57] ABSTRACT

A compound consisting of three aromatic moieties respectively bonded to a methyl carbocation, and a counterion; wherein each of the three aromatic moieties is optionally substituted with an electron-donating group, at least one of the three aromatic moieties is bonded to a metal complex moiety, either directly or through a linker, and the methyl carbocation, the aromatic moieties, the metal complex moiety, and the linker form a conjugated system.

22 Claims, No Drawings

ORGANOMETALLIC COMPOUNDS

BACKGROUND OF THE INVENTION

Compounds which absorb in the near-infrared region (from about 700 nm to about 1200 nm) have recently generated much interest due to their use in laser optical recording, laser printing, and laser thermal writing display. In addition to these applications, such compounds are also useful in IR photography and photodynamic therapy. See, e.g., M. Matsuoka, *Infrared Absorbing Dyes,* Plenum Press, New York, 1990 and J. Fablan, H. Nakazumi, M. Matsuoka, *Chem. Rev.* 1992, 92, 1197.

SUMMARY OF THE INVENTION

This invention features an organometallic compound consisting of (1) three aromatic moieties respectively bonded to a methyl carbocation, and (2) a counterion. Each of the three aromatic moieties is optionally substituted with an electron-donating group. Further, at least one of the three aromatic moieties is bonded to a metal complex moiety, either directly or through a linker. The methyl carbocation, the aromatic moieties, the metal complex moiety, and the linker (if present) together form a conjugated system. Examples of a counterion that can be present in the organometallic compounds of this invention include tetrafluoroborate, tetraphenylborate, hexafluorophosphate, acetate, perchlorate, carboxylate, and halides.

Aromatic moieties include single ring and fused ring moieties, which can be aryls or heteroaryls (i.e., aromatic rings containing heteroatoms such as nitrogen, oxygen, or sulfur). Some examples of aromatic moieties are phenyl, pyridinyl, furanyl, thienyl, pyrrolyl, naphthalenyl, and azulenyl.

The term "electron-donating group" refers to non-metallic moieties that have delocalizable electrons. Examples of an electron-donating group include alkoxy, (e.g., methoxy, ethoxy, or butoxy) and amino (e.g., methylamino, dimethylamino, or isopropylethylamino).

A metal complex moiety refers to an organic moiety bonding or coordinating to a metal atom such as a transition metal atom, e.g., Ru, Fe, Ni, or Pt. Such an organic moiety, commonly known as a ligand, can be either a bridging or a non-bridging ligand. A bridging ligand coordinates to the metal ion and is bonded directly or indirectly to one of the three aromatic moieties of a compound of this invention. In other words, a bridging ligand serves as a bridge between a metal ion and an aromatic moiety. As a bridging ligand forms a part of the conjugated system between the metal ion and the aromatic moiety, it has to be electronically conjugated. Examples of such a ligand include cyclic conjugated ligands (e.g., cyclopentadienyl, methylcyclopentadienyl, phenyl, indenyl, fluorenyl), and unsaturated acyclic hydrocarbons (e.g., alkynyl ligands or allyl ligands). On the other hand, a non-bridging ligand is not required to be electronically conjugated. Examples of non-bridging ligands include phosphine ligands (e.g., PPh$_2$(CH$_2$)$_2$PPh$_2$ or PPh$_3$), amine ligands (e.g., NMe$_3$ or NEt$_3$), and alkyl ligands (e.g., methyl, ethyl, or isopropyl).

Similar to the bridging ligand, supra, the optional linker between the aromatic moiety and the metal complex is also required to be electronically conjugated. Some examples of such a linker are polyenes (e.g., —(CH=CH)$_3$—), aromatic moieties (e.g., phenyl), or a combination of both (e.g., a thienylvinyl).

In one embodiment, the organometallic compound of this invention has the following formula:

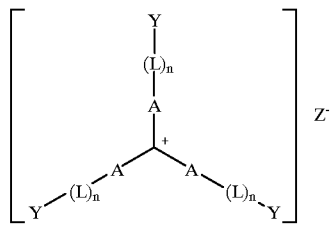

wherein each A, independently, is an aromatic fused ring or

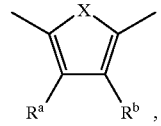

in which X is —O—, —S—, —NH—, —N(alkyl)-, or —C(R$^c$)=C(R$^d$)—, and each of R$^a$, R$^b$, R$^c$, and R$^d$, independently, is H, alkyl, alkoxy, or NR$^1$R$^2$ with each of R$^1$ and R$^2{}_1$, independently, being H or alkyl; each L is an electronically conjugated linker moiety; each n, independently, is 0, 1, 2, or 3; each Y, independently, is H, alkoxy, NR$^3$R$^4$, or a Ru, Fe, Ni, or Pt metal complex, wherein R$^3$ and R$^4$, independently, is H, alkyl, cycloalkyl, heterocycloalkyl, aryl, or heteroaryl; and Z is a counterion.

Examples of the organometallic compounds of this invention include [(Cp)Ru(PPh$_3$)$_2$(α—C≡C)—C$_6$H$_4$—C$^+$—(C$_6$H$_4$—NEt$_2$—p)$_2$)][BF$_4{}^-$], [(Cp)Ru(PPh$_3$)$_2$(α—C≡C)—th—(E)—CH=CH—th—C$^+$—(C$_6$H$_4$NEt$_2$—p)$_2$)] [BF$_4{}^-$], [((Cp)Ru(PPh$_3$)$_2$(α—C≡C)—C$_6$H$_4$)$_2$—C$^+$—(C$_6$H$_4$—NMe$_2$—p)] [BF$_4{}^-$], and [((Cp)Ru(PPh$_3$)$_2$(α—C≡C—C$_6$H$_4$))$_3$—C$^+$][BF$_4{}^-$], wherein Cp is cyclopentadienyl, Ph is phenyl, th is 2,5-thienyl, Me is methyl, and Et is ethyl.

The term "alkyl" refers to a straight or branched hydrocarbon chain containing 1 to 4 carbon atoms. Examples of alkyl include, but are not limited to, methyl, ethyl, propyl, isopropyl, butyl, isobutyl, sec-butyl, tert-butyl groups. By "alkoxy" is meant —O—C$_{1-4}$ alkyl. A cycloalkyl group is a saturated hydrocarbon ring moiety containing 3 to 8 carbon atoms. Some examples of cycloalkyl are cyclopropyl, cyclopentyl, and cyclohexyl. Heterocycloalkyl are 3–8 membered cycloalkyl moieties containing heteroatoms, e.g., nitrogen, oxygen, or sulfur. Examples of heterocycloalkyl include tetrahydrofuranyl, tetrahydropyranyl, piperidinyl, morpholino and pyrrolindinyl. Some examples of aryl are phenyl and naphthalenyl and some examples of heteroaryl are pyridinyl, furanyl, thienyl, and pyrrolyl.

DETAILED DESCRIPTION OF THE INVENTION

The invention features novel organometallic compounds. Compounds of this invention which absorb in the near-infrared (near-IR) region can be used in laser optical recording systems, laser printing systems, laser thermal writing display, and infrared photography.

The design of the organometallic compounds of this invention is based on the electronically conjugated system that is formed between (1) an electron-accepting carbocation which is bonded to three aromatic moieties (e.g., a triphenyl carbocation or a diphenylthienyl carbocation) and (2) one or more electron-donating metal complex (e.g., a ruthenium s-acetylide complex or a ferrocenyl complex). An electronically conjugated linker, e.g., thienylvinyl, can be optionally inserted between one of the three aromatic moieties and a metal complex. Rigid annulated rings can also be included in the linker to enhance rigidity of the compounds. Further, non-metallic electron-donating groups, e.g., dialkylamino groups, can be bonded to the aromatic moieties to stabilize the carbocation. As the near-IR absorbing property of the compounds depends on the charge-transfer activities between the carbocation and the metal complex, it is important to introduce electron-donating groups at certain positions on the aromatic rings so that electrons from these groups can participate in the conjugated system. For example, the electrons of an dialkylamino group can only delocalize into the system if the dialkylamino group is placed at the para or the ortho position with respect to the position where the carbocation is bonded to the aromatic moiety.

One method of preparing the organometallic compounds of this invention is shown in Scheme 1 below:

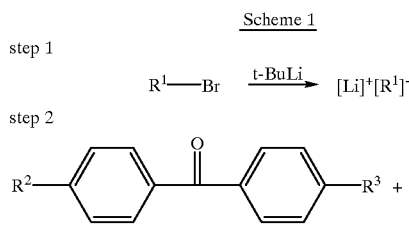

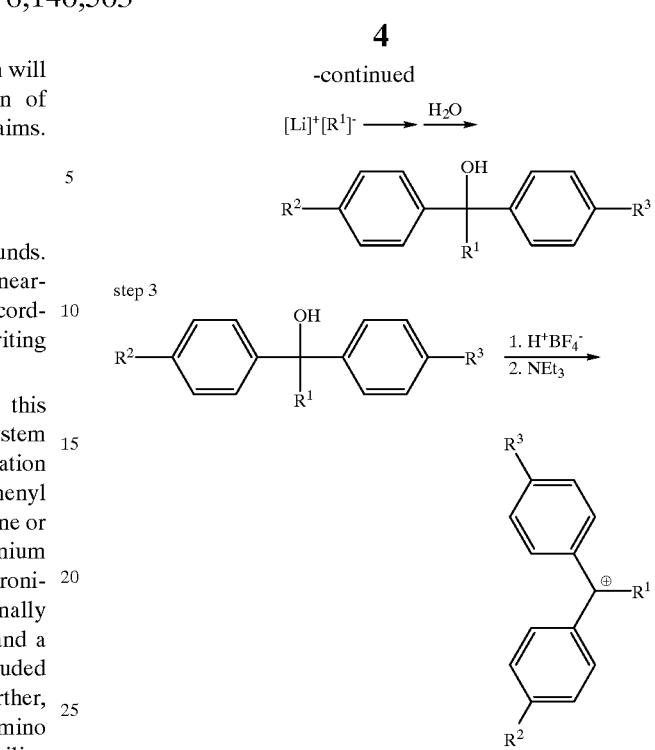

In step 1, an aryl halide is converted into its respective anion by reacting with a strong base such as t-butyllithium. The aryllithium salt resulted can then be reacted with a metal complex-containing diaryl ketone to form a triaryl carbinol in step 2. Formation of the carbocation product can be obtained from protonation of the carbinol by an acid, e.g., $HBF_4$, followed by treatment with triethylamine ($NEt_3$) in step 3.

As shown below, the metal complex-containing diaryl ketone in step 2, e.g., $(PPh_3)_2CpRu$—C≡C—Ph—C(=O)—Ph—C≡C—$RuCp(PPh_3)_2$, can be prepared from the reaction of $CpRu(PPh_3)_2Cl$ with 4,4'-diethnylbenzonone according to the procedure described in M. I. Bruce, A. G. Swincer, *Adv. Organomet. Chem.* 1983, 22, 59; M. I. Bruce, *Chem. Rev.* 1991, 91, 270; and J. Manna, K. D. John, M. D. Hopkins, *Adv. Organomet. Chem.* 1995, 38, 79:

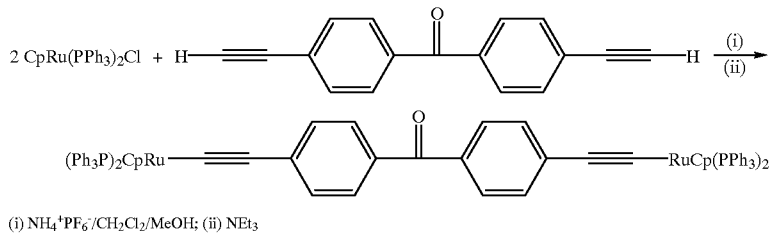

(i) $NH_4^+PF_6^-/CH_2Cl_2/MeOH$; (ii) $NEt_3$

An alternative method to prepare organometallic compounds of this invention is shown in Scheme 2 below:

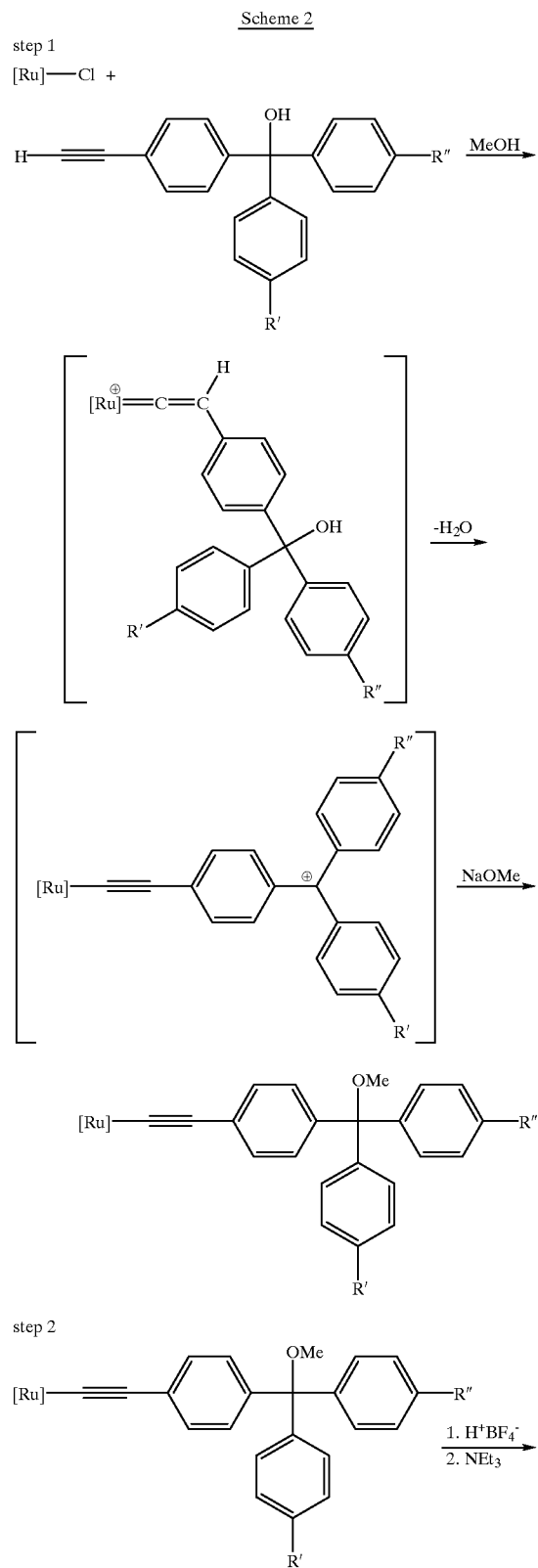
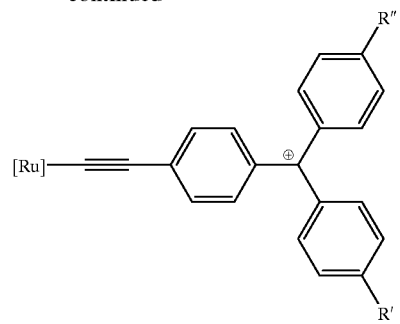

The method set forth in Scheme 2 is particularly suitable for preparing sterically congested compounds, e.g., compounds with three metal complexes, which may be difficult to prepare using the method above.

A triaryl carbinol is formed prior to the bonding of the metal complex moieties to the aryls in this method. Intermediates such as methyl(triphenylmethyl)ether can be formed by converting the hydroxyl group of the carbinol to a methoxy group using reagents such as sodium methoxide. See step 1 below. Step 2 employs the same reagents as those shown in step 3 of Scheme 1, i.e., $HBF_4$ and $NEt_3$, to form the carbocation. Note that the term "aryl" used in the above methods covers both aryl and heteroaryl.

Without further elaboration, it is believed that one of ordinary skill in the art can, based on the description herein, utilized parts or the whole procedure to its full extent. The following specific examples are, therfore, to be construed as merely illustrative, and not limitative of the remainder of the disclosure in any way whatsoever. All publications mentioned above and in the examples are incorporated by reference in their entirety.

The reactions and manipulations described in the examples below were carried out under $N_2$ with the use of standard inert atmosphere and Schlenk techniques. Solvents were dried by standard procedures. Column chromatography was performed with the use of silica gel (230–400 mesh ASTM, Merck) as the stationary phase in a column 35 cm in length and 2.5 cm in diameter. Compounds $Cp(PPh_3)_2Ru$ ($C\equiv C-C_6H_4Br-p$), $Cp(PPh_3)_2Ru(C\equiv C-th-$ (E)— $CH=CH-th-Br$), $Cp(PPh_3)_2RuCl$, $PdCl_2(PPh_3)_2$, 4,4,'-diethynylbenzophenone, and (4-bromophenylethynyl)trimethylsilane were prepared by procedures described in Bruce et al., *J. Organomet. Chem.* 1987, 320, 217; Hsung et al., *Organometallics* 1995, 14, 4808; Bruce et al., *Inorg. Chem.* 1990, 28, 270; Colquhoun et al., Eds., *New Pathway for Organic Synthesis* Plenum Press: New York, 1984; chapter 9; Royles et al., *J. Chem. Soc., Perkin Trans.* 1 1994, 255; and Steinmetz et al., *J. Am. Chem. Soc.* 1994, 116, 932; respectively. Infrared spectroscopy was performed using a Perkin-Elmer 880 spectrometer. The NMR spectra were recorded on Bruker AMX400 ($^1H$, $^{13}C$, $^{31}P$) and AC300 ($^1H$, $^{31}P$) spectrometers. Electronic absorption spectra were obtained on a Perkin-Elmer Lambda 9 spectrometer. Mass spectra (EI) were recorded on a VG70-250S mass Spectrometer. Elemental analyses were performed on a Perkin Elmer 2400 CHN analyzer.

The organometallic compounds described in Examples 1–3 and Examples 4–6 were prepared according to the previously described Schemes 1 and 2, respectively.

EXAMPLE 1

Synthesis of [Cp(PPh$_3$)$_2$Ru(C≡C—C$_6$H$_4$C(C$_6$H$_4$NEt$_2$-p$_2$)] [BF$_4$]

A solution of t-BuLi (0.71 mL, 1.21 mmol, 1.7 M in pentane) was added to a solution of Cp(PPh$_3$)$_2$Ru(C≡CC$_6$H$_4$Br-p) in 25 mL of Et$_2$O that was prechilled to −78° C. The solution was then stirred at −30° C. for 15 minutes. After the solution was further warmed to room temperature and stirred for 30 more minutes, 4,4'-bis(diethylamino)benzophenone (0.35 g, 1.1 mmol) in 20 mL of THF was slowly added and stirred for 16 hours. After addition of 1 mL of H$_2$O, the solvent was removed in vacuo and the residue extracted with CH$_2$Cl$_2$. The extract was filtered through celite and concentrated. Yellow powders formed upon addition of hexane. The powders were collected and dried to provide Cp(PPh$_3$)$_2$Ru(C≡CC$_6$H$_4$)C(OH) (C$_6$H$_4$NEt$_2$-p)$_2$ in 70% yield. $^1$H NMR (300 MHz, CD$_3$CN, 25° C., TMS) : δ=1.10 (t, J=7.0 Hz, 12 H, CH3), 3.31 (q, 8 H, CH$_2$), 4.28 (s, 5 H, Cp), 6.62 (d, J=8.9 Hz, 4 H, NC$_6$H$_4$), 6.97 (d, NC$_6$H$_4$), 7.10–7.46 (m, 34 H, PPh$_3$ and C$_6$H$_4$); $^{31}$P NMR (120 MHz, CD$_3$CN, 25° C., 85% H$_3$PO$_4$): δ=48.6. This crude compound was dissolved in 25 mL of THF and cooled to 0° C. A solution of HBF$_4$ (0.30 mL, 54% in Et$_2$O) was added, and the resulting mixture was stirred for 5 minutes. Et$_3$N (1 mL) was added, and the resulting green solution was pumped dry. The residue was first washed with Et$_2$O/hexane (1:1) until the washing was clear, then washed rapidly with H$_2$O and dried. Recrystallization of the crude product from CH$_2$Cl$_2$/hexane afforded green powdery product, [Cp(PPh$_3$)$_2$Ru(C≡C—C$_6$H$_4$C(C$_6$H$_4$NEt$_2$-p$_2$)] [BF$_4$], in 68% yield (0.81 g). Anal. Calcd for C$_{70}$H$_{67}$BF$_4$N$_2$P$_2$Ru: C 70.88, H 5.69. Found C 70.67, H 5.71. mp=176° C. $^1$H NMR (300 MHz, CD$_3$CN, 25° C., TMS): δ=1.26 (t, J=7.1 Hz, 12 H, CH$_3$), 3.60 (q, 8 H, CH$_2$), 4.41 (s, 5H, Cp), 6.94 (d, J=9.4 Hz, 4 H, NC$_6$H$_4$), 7.14–7.43 (m, 38H, PPh$_3$ and C$_6$H$_4$); 45.4 (CH$_2$), 86.1 (Cp), 110.0 (Ru—C≡C$_\beta$), 112.8 (NC$_6$H$_4$), 121.9 (C$_6$H$_4$), 126.6 (NC$_6$H$_4$), 127.5 (C$_{meta}$ of PPh$_3$), 128.9 (C$_{para}$ of PPh$_3$), 130.4 (C$_6$H$_4$), 133.8 (C$_{ortho}$ of PPh$_3$), 136.2 (C$_6$H$_4$), 137.5 (C$_6$H$_4$), 138.5 (t, J$_{c-p}$=21.1 Hz, C$_{ipso}$ of PPh$_3$), 140.4 (NC$_6$H$_4$), 146.0 (t, J$_{c-p}$=24.6 Hz, Ru—C≡C$_\alpha$), 154.6 (NC$_6$H$_4$), 176.7 (CPh$_3$); $^{31}$P NMR (120 MHz, CD$_3$CN, 25° C., 855 H$_3$PO$_4$): δ=48.5; IR (KBr, cm$^{-1}$): 1073 (s, BF$_4$), 2017 (s, C≡C): VIS/NIR (CH$_2$Cl$_2$) λ$_{max}$ (nm), ε=8.25, f=0.62; 725 nm, ε=3.79, f=0.49.

EXAMPLE 2

(i) Synthesis of [Cp(PPh$_3$)$_2$Ru(C≡CC$_6$H$_4$)]C(O)

To a flask containing a mixture of 4,4'-dibromobenzophenone (5.0 g, 14.7 mmol), PdCl$_2$(PPh$_3$)$_2$ (0.42 mg, 0.60 mmol), and CuI (60 mg, 0.30 mmol) was added THF (100 mL), $^i$Pr$_2$NH (20 mL) and trimethylsilylacetylene (4.6 mL, 32.5 mmol) under a nitrogen atmosphere. The mixture was stirred at room temperature for 40 hours. The solvent was removed under vacuum, and the residue was extracted with CH$_2$Cl$_2$/H$_2$O. The organic layer was collected, dried over MgSO$_4$, filtered through Al$_2$O$_3$, and pumped dry. The residue was recrystallized from CH$_2$Cl$_2$/hexane at −30° C. to afford pale brown crystalline 4,4'-bis(trimethylsilylethynyl)benzophenone in 96% yield (5.29 g). $^1$H NMR (300 MHz, C$_6$D$_6$, 25° C., TMS): δ=0.25 (s, 18 H, CH$_3$), 7.53 (d, J=8.6 Hz, 4 H, C$_6$H$_4$), 7.69 (d, 4 H, C$_6$H$_4$). To a mixture of 4,4'-bis(trimethylsilylethynyl)benzophenone (1.0 g, 2.67 mmol) and KOH (0.30 g, 5.36 mmol) was added 50 mL of MeOH and the solution was stirred at room temperature for 3 hours. The solution was then extracted with Et$_2$O. The Et$_2$O solution was pumped dry and the residue was chromatographed using EtOAc/hexane (1:50 to 1:5) as eluent to afford 4,4'-diethynylbenzophenone in 68% yield (0.42 g).

To a mixture of Cp(PPh$_3$)$_2$RuCl (1.45 g, 2.0 mmol), 4,4'-diethynylbenzophenone (0.23 g, 1.0 mmol and NH$_4$$^+$ PF$_6$$^-$ (0.33 g, 2.1 mmol) was added 50 mL of MeOH and 40 mL of CH$_2$Cl$_2$. The resulting mixture was refluxed for 3 h. The solution was cooled to room temperature and 3 mL of Et$_3$N was added. After the solvent was removed, the residue was chromatographed using EtOAc/hexane (1:5) as eluent to afford [Cp(PPh$_3$)$_2$Ru(C≡CC$_6$H$_4$)]C(O) as a yellow powder was in 65% yield (1.05 g). Anal. Calcd for C$_{99}$H$_{78}$OP$_4$Ru$_2$: C 73.87, H 4.88. Found C 73.50, H 4.49. $^1$H NMR (300 MHz, CD$_3$CN, 25° C., TMS): δ=4.39 (s, 10 H, Cp), 7.16–7.54 (m, 60 H, PPh$_3$), 7.21 (d, J=8.3 Hz, 4 H, C$_6$H$_4$), 7.61 (d, 4 H, C$_6$H$_4$); $^{13}$C NMR (100 MHz, CDCl$_3$, 25° C., TMS): δ=85.4 (Cp), 116.0 (Ru—C≡C$_\beta$), 127.2 (t, J$_{C-P}$=24.6 Hz, Ru—C$_\alpha$≡C), 127.3 (C$_{meta}$ of PPH$_3$), 128. 5 (C$_{para}$ of PPh$_3$), 129.9 (C$_6$H$_4$), 130.1 (C6H4), 132.6 (C$_6$H$_4$), 133.8 (t, J$_{C-P}$=5.1 Hz, C$_{ortho}$ of PPh$_3$), 134.5 (C$_6$H$_4$), 138.7 (t, J$_{C-P}$=20.9 Hz, C$_{ipso}$ of PPh$_3$), 195.7 (CO); $^{31}$P NMR (120 MHz, CD$_3$CN, 25° C., 85% H$_3$PO$_4$): δ=48.7; IR (KBr, cm$^{-1}$): 1640 (m, CO), 2062 (vs, C≡C).

(ii) Synthesis of [((Cp)Ru(PPh$_3$)$_2$(α—C≡C)—C$_6$H$_4$)$_2$—C$^+$—(C$_6$H$_4$—NMe$_2$-p)] [BF$_4$$^-$]

A solution of t-BuLi (0.78 mL, 1.33 mmol, 1.7 M in pentane) was added to a solution of 4-bromo-N,N-dimethylaniline (0.12 g, 0.60 nmol) in 20 mL of THF prechilled to −78° C. The solution was then stirred at −30° C. for 15 minutes. The solution was further warmed to room temperature and stirred for 30 minutes. This solution was slowly added to a solution of [Cp(PPh$_3$)$_2$Ru(C≡CC$_6$H$_4$)]$_2$CO (0.80 g, 0.50 mmol) in 20 mL of THF, and the mixture was stirred at room temperature for 16 hours. After addition of 1 mL of H$_2$O, the solvent was removed in vacuo and the residue extracted with CH$_2$Cl$_2$. The extract was filtered through Celite and concentrated. A yellow powder formed upon addition of hexane. The powder was collected and dried to provide [(Cp(PPh$_3$)$_2$Ru(C≡CC$_6$H$_4$))$_2$C(OH) (C$_6$H$_4$NMe$_2$)] in 65% yield. $^1$H NMR (300 MHz, CDCl$_3$, 25° C., TMS) : δ=2.63 (s, 6 H, CH$_3$), 4.56 (s, 10 H, Cp), 6.54 (d, J=8.9 Hz, 2 H, NC$_6$H$_4$), 7.54 (d, 2 H, NC$_6$H$_4$), 7.61 (d, J=8.5 Hz, 4 H, C$_6$H$_4$), 7.68 (d, 4 H, C$_6$H$_4$), 7.02–7.83 (m, 60 H, PPh$_3$); $^{31}$P NMR (120 MHz, CDCl$_3$, 25° C., 85% H$_3$PO$_4$): δ−50.3. This crude compound was dissolved in 25 mL of THF and cooled to 0° C. A solution of HBF$_4$ (0.20 ML, 54% in Et$_2$O) was added, and the resulting mixture was stirred for 5 minutes. Et$_3$N (1 mL) was added, and the resulting green solution was pumped dry. The residue was first washed with Et$_2$O/hexane (1:1) until the washing was clear, then washed rapidly with H$_2$O and dried. Recrystallization of the crude product from CH$_2$Cl$_2$/hexane afforded green powdery [((Cp) Ru(PPh$_3$)$_2$ (α—C≡C)—C$_6$H$_4$)$_2$—C$^+$—(C$_6$H$_4$—NMe$_2$-p)] [BF$_4^-$] in 74% yield (0.67 g). Anal. Calcd. for C$_{107}$H$_{88}$BF$_4$NP$_4$Ru$_2$: C 71.37, H 4.93, N 0.78. Found; C 70.98, H 4.82, N 0.59. mp=185° C. $^1$H NMR (300 MHz, CD$_3$CN, 25° C., TMS): δ=3.29 (s, 10 H, Cp), 6.99 (d, J=9.3 Hz, 2 H, NC$_6$H$_4$), 7.12–7.44 (m, 68 H, PPh$_3$ and C$_6$H$_4$), 7.51 (d, 2 H. NC$_6$H$_4$). $^{13}$C NMR (100 MHz, CD$_3$CN, HMBC & HMQC, 25° C., TMS): δ=40.8 (CH$_3$), 86.6 (Cp), 113.3 (NCCH), 127.5 (C$_{meta}$ of PPh$_3$), 128.2 (NCCHCHC), 128.3 (Ru—C≡C$_\beta$), 128.9 (C$_{para}$ of PPh$_3$), 131.2 (C≡CCCH), 133.6 (C$_{ortho}$ of PPh$_3$), 134.1 (C≡CC), 136.8 (C≡CCCHCH), 138.0 (t, J$_{C-P}$=21.4 Hz, C$_{ipso}$ of PPh$_3$), 139.3 (C≡CCCHCHC), 140.6 (NCCHCH), 156.5 (CH$_3$NC), 158.7 (t, J$_{C-P}$=24.6 Hz, Ru—C$_\alpha$≡C), 176.7 (C(C$_6$H$_4$)$_3$); $^{31}$P NMR (120 MHz, CD$_3$CN, 25° C., 85% H$_3$PO$_4$): δ=48.4; IR (KBr, cm$^{-1}$): 1085 (m, BF$_4$), 1995 (vs, C≡C), 2035 (sh, C≡C) VIS/NIR (CH$_2$Cl$_2$) λ$_{max}$ (nm), ε(10$^4$M$^{-1}$cm$^{-1}$): 740 nm, ε=6.78, f=1.08; 855 nm, ε=7.74, f=0.84.

EXAMPLE 3

Synthesis of [Cp(PPh$_3$)$_2$Ru (C≡C—th—(E)—CH=CH—th—C(C$_6$H$_4$NEt$_2$)$_2$] [BF$_4$]

[Cp(PPh$_3$)$_2$Ru(C≡C-th- (E)—CH=CH—th—C (C$_6$H$_4$NEt$_2$)$_2$] [BF$_4$] was synthesized by the same procedure as described in Example 1 except that Cp(PPh$_3$)$_2$Ru(C≡C-th- (E)—CH=CH-th-Br) was used instead of Cp(PPh$_3$)$_2$Ru (C≡CC$_6$H$_4$Br—p). Dark blue powdery product was isolated in 70% yield. Anal. Calcd for C$_{74}$H$_{69}$BF$_4$N$_2$P$_2$S$_2$Ru: C 68.35, H 5.35, N 2.15. Found: C 68.20, H 5.22, N 2.07. T$_{decmp}$=156° C. $^1$H NMR (300 MHz, CD$_3$CN, 25° C., TMS): δ=1.25 (t, $^3$J=6.8 Hz, 12 H, CH$_3$), 3.59 (q, 8 H, CH$_2$), 4.36 (s, 5 H, Cp), 6.54 (d, J=3.8 Hz, 1 H, SCCH), 6.94 (d, J=9.3 Hz, 4 H, C$_6$H$_4$), 6.97 (d, 1 H, J=16.5 Hz, 1 H, =CH), 7.09–7.50 (m, 38 H, PPh$_3$, =CH, SCCH, and C$_6$H$_4$). $^{13}$C NMR (100 MHz, CD$_3$CN, 25° C., TMS): δ=12.0 (CH$_3$), 45.3 (CH$_2$), 85.8 (Cp), 110.0 (Ru—C≡C$_\beta$), 110.6 (NC$_6$H$_4$), 124.8 (SC=), 125.5 (NC$_6$H$_4$), 127.3 (C$_6$H$_4$), 127.4 (C$_6$H$_4$), 127.5 (t, J$_{c-p}$=4.6 Hz, C$_{meta}$ of PPh$_3$), 128.3 (C$_6$H$_4$), 128.8 (C$_6$H$_4$), 128.9 (C$_{para}$, of PPh$_3$), 133.6 (NC$_6$H$_4$), 134.0 (SC=), 138.6 (t, J$_{c-p}$=21.0 Hz, C$_{ipso}$ of PPh$_3$), 139.3 (t, J$_{c-p}$=24.0 Hz, Ru—C$_\alpha$≡C), 146.8 (SC= or C(C$_6$H$_4$)$_2$th), 153.1 (C(C$_6$H$_4$)$_2$th or SC=), 154.1 (NC$_6$H$_4$); $^{31}$P NMR (120 MHz, CD$_3$CN, 25° C., 85% H$_3$PO$_4$): δ=48.0; IR (KBr, cm$^{-1}$): 1085 (m, BF$_4$), 2009 (vs, C≡C): VIS/NIR (CH$_2$Cl$_2$) λ$_{max}$(nm), ε(10$^4$M$^{-1}$CM$^{-1}$) 897 nm, ε=6.74, f=0.88.

EXAMPLE 4

(i) Synthesis of Cp(PPh$_3$)$_2$Ru(C≡CC$_6$H$_4$C(OMe)Ph$_2$)

To a flask containing a mixture of 4-bromobenzophenone (1.31 g, 5.0 mmol). PdCl$_2$(PPh$_3$)$_2$ (70 mg. 0.10 mmol), and CuI (10 mg, 0.050 mmol) was added Et$_2$NH (50 mL) and trimethylsilyl-acetylene (0.85 mL, 6.0 mmol) under a nitrogen atmosphere. The mixture was stirred at room temperature for 5 h. The solvent was removed under vacuum, and the residue was extracted with CH$_2$Cl$_2$/H$_2$O. The organic layer was collected, dried over MgSO$_4$, filtered through Al$_2$O$_3$, and pumped dry. The residue was recrystallized from CH$_2$Cl$_2$/hexane to afford pale brown crystalline 4-(trimethylsilylethynyl)benzophenone in 93% yield (1.30 g). $^1$H NMR (300 MHz, C$_6$D$_6$, 25° C., TMS): δ=0.25 (s, 9 H, CH$_3$) 7.44–7.74 (m 9 H, Ph and C$_6$H$_4$); MS (EI) : m/e 278 (M$^+$—CH$_3$) To a Et$_2$O solution (100 mL) of 4-(trimethylsilylethynyl)benzophenone (1.39 g, 5.0 mmol) prechilled to −30° C. was slowly added a solution of phenyllithium (3.33 mL, 6.0 mmol, 1.8 M in cyclohexane-ether). The solution was slowly warmed to room temperature and stirred for 4 hours. 1 mL of H$_2$O was added and the solution was stirred for 30 minutes. Additional H$_2$O (>200 mL) was added and the organic layer was collected, dried over MgSO$_4$, filtered through Al$_2$O$_3$, and pumped dry. The residue was chromatographed using CH$_2$Cl$_2$/hexane (2:1) as eluent to afford (4-ethynylphenyl)-diphenylmethanol as a pale yellow oil in 81% yield (1.24 g).

To a mixture of Cp(PPh$_3$)$_2$RuCl (0.36 g, 0.50 mmol) and (4-ethynylphenyl)diphenylmethanol (0.16 g, 0.56 mmol) was added 50 mL of MeOH. The resulting mixture was refluxed for 3 hours. The solution was cooled to 0° C. and Na (18 mg, 0.90 mmol) was added slowly. The solution was filtered and the yellow solid was washed with MeOH (3×10 mL) and hexane (3×5 mL). The crude product was recrystallized from CH$_2$Cl$_2$/hexane to afford Cp(PPh$_3$)$_2$Ru (C≡CC$_6$H$_4$C(OMe)Ph$_2$) as a yellow powder in 77% yield (0.38 g). Anal. Calcd for C$_{63}$H$_{52}$OP$_2$Ru: C 76.58, H 5.30. Found C 76.31, H 5.21. $^1$H NMR (s, 5 H, Cp), 7.51 (d, J=8.4 Hz, 2 H, C$_6$H$_4$), 7.56 (d, 2 H, C$_6$H$_4$), 6.88–7.10 and 7.62–7.74 (m, 40 H, PPh$_3$ and Ph); $^{13}$C NMR (100 MHz, CDCl$_3$, 25° C., TMS): δ=52.0 (OCH$_3$), 85.2 (Cp), 87.1 (C(C$_6$H$_4$)Ph$_2$), 114.3 (Ru—C≡Cβ), 116.9 (t, J$_{c-p}$=24.0 Hz, Ru—C$_\alpha$≡C), 126.6 (Ph), 127.2 (t, J=4.5 Hz, C$_{meta}$ of PPh$_3$), 127.6 (Ph), 128.4 (C$_{para}$), 128.6 (Ph), 128.7 (C$_6$H$_4$), 129.3 (C$_6$H$_4$), 129.7 (C$_6$H$_4$), 133.8 (t, J$_{c-p}$=5.0 Hz, C$_{ortho}$ of PPh$_3$, 137.4 (C$_6$H$_4$), 138.9 (t, J$_{c-p}$=20.7 Hz, C$_{ipso}$ of PPh$_3$), 144.8 (Ph); $^{31}$P NMR (120 MHz, C$_6$D$_6$, 25° C., 85% H$_3$PO$_4$): δ=51.5; IR (KBr, cm$^{-1}$): 1089 (s, C—O) , 2073 (vs, C≡C).

(ii) Synthesis of [Cp (PPh$_3$)$_2$Ru(C≡CC$_6$H$_4$C (C$_6$H$_4$-p) Ph)] [BF$_4$]

Excess HBF (54% Et$_2$O solution) was slowly added to a THF solution of Cp(PPh$_3$)$_2$Ru(C≡CC$_6$H$_4$C(OMe)Ph$_2$) prechilled to 0° C. The resulting mixture was stirred for 5 minutes, and Et$_3$N was added. The product formed was characterized by electronic spectra only due to its air sensitivity.

EXAMPLE 5

Synthesis of [Cp(PPh$_3$)$_2$Ru(C≡CC$_6$H$_4$C(C$_6$H$_4$—OMe-p)Ph)] [BF$_4$]

The organometallic compound, [Cp(PPh$_3$)$_2$Ru (C≡CC$_6$H$_4$C(C$_6$H$_4$—OMe-p)Ph)] [BF$_4$] was prepared in a similar manner as described in Example 4, except that (4-methoxy)phenyllithium (which was prepared in situ from 4-bromoanisole and t-BuLi) was utilized instead of phenyllithium. Although the final product was characterized by electronic spectra only (due to its air sensitivity), the methylether intermediate, (4-ethynylphenyl) (4'-methoxypheny) phenylmethanol, was isolated and characterized as shown below:

Anal. Calcd for $C_{22}H_{18}O_2$: C 84.05, H 5.77. Found C 84.04, H 5.81 $^1$H NMR (300 NHz, CDCl$_3$, 25° C., TMS): $\delta$=2.70 (br, 1 H, OH), 3.04 (s, 1 H, ≡CH), 3.78 (s, 3 H, OCH$_3$), 6.81 (d, J=8.3 Hz, 2 H, C$_6$H$_4$—O), 7.13 (d 2 H, C$_6$H$_4$—O), 7.21–7.29 (m, 7 H, Ph and C$_6$H$_4$), 7.41 (d, J=8.4 Hz, 2 H, C$_6$H$_4$. 2: Anal. Calcd for $C_{64}H_{54}O_2P_2Ru$: C 75.50, H 5.35. Found C 75.36, H 5.24. $^1$H NMR (300 NHz, C$_6$D$_6$, 25° C., TMS): $\delta$=3.13 (s, 3 H, OCH$_3$), 3.32 (s, 3 H, OCH$_3$), 4.49 (s, 5 H, Cp), (d, J=8.8 Hz, 2 H, C$_6$H$_4$—O), 7.55 (d, 2 H, C$_6$H$_4$—O), 7.61 (d, J=8.8 Hz, 2 H, C$_6$H$_4$), 7.64 d, 2 H, C$_6$H$_4$), 6.90–7.23, 7.71–7.77 (M, 35 H, PPh$_3$ and Ph), ; $^{31}$P NMR (120 NHz, C$_6$D$_6$), 25° C., 85% H$_3$PO$_4$: $\delta$32 51.6; IR (KBr, cm$^{-1}$): 1089, 1178 (s, C—O), 2073 (vs, C≡C).

EXAMPLE 6

Synthesis of [{CP(PPh$_3$)$_2$Ru(C≡CC$_6$H$_4$)}$_3$C] [BF$_4$]

A solution of n-BuLi (2.1 mL, 3.36 mmol, 1.6 M in hexane) was added to a solution of (4-bromophenylethynyl)trimethylsilane (0.69 mg, 2.74 mmol) in 50 mL of Et$_2$O prechilled to −78° C. The solution was then stirred at −30° C. for 15 minutes. The solution was warmed to room temperature, stirred for 1 hour, and cooled to −30° C. A THF solution (20 mL) of 4,4'-bis(trimethylsilylethynyl)benzophenone (0.83 g, 2.19 nmol) prechilled to −30° C. was added slowly and the resulting mixture was stirred for 15 minutes. The solution was warmed to 0° C. and stirred for 2 hours. After addition of 1 mL of H$_2$O the solution was pumped dry. The residue was chromatographed using CH$_2$Cl$_2$/hexane (1:5 to 2:1) as eluent to afford tri(4-(trimethylsilylethynyl)phenyl)methanol as a colorless powder in 77% yield (0.92 q). $^1$H NMR (300 MHz, CDCL$_3$, 25° C., TMS): 0.22 (s, 27 H, CH$_3$), 2.72 (s, 1 h, OH), 7.13 (d, J=8.4 Hz, 6 H, C$_6$H$_4$), 7.38 (d, 6 H, C$_6$H$_4$). To a mixture of tri (4-(trimethylsilylethynyl)phenyl)methanol (0.92 g, 1.68 mmol) and KOH (0.28 g, 5.0 mmol) was added 50 mL of MeOH and the solution was stirred at room temperature for 3 hours. The solution was then extracted with Et$_2$O solution was pumped dry and the residue was chromatographed using EtOAc/hexane (1:50 to 1:5) as eluent to afford tri(4-ethynylphenyl)methanol as a colorless powder in 84% yield (0.47 g). Anal. Calcd for $C_{34}H_{40}Si_3O$: C 74.39, H 7.34. Found: C 74.03, H 7.28. $^1$H NMR (300 MHz, CDCl$_3$, 25° C., TMS) : 2.73 (s, 1 H, OH), 3.06 (s, 3 H, ≡CH), 7.19 (d, J=8.2 Hz, 6 H, C$_6$H$_4$), 7.43 (d, 6 H, C$_6$H$_4$) ; IR (KBr, cm$^{-1}$): 1018 (m, C—O), 2107 (w, C≡C); 3554 (m, O—H).

To a mixture of Cp(PPh$_3$)$_2$RuCl (1.20 g. 1.65 mmol), tri(4-ethynylphenyl)methanol (166 mg, 0.50 mmol) and Tl$^+$PF$_6$— (0.55 g, 1.58 mmol) was added 30 mL of MeOH and 20 mL of THF. The resulting mixture was heated at 80° C. for 3.5 hours. The solution was cooled to room temperature and a solution NaOMe, prepared in situ from Na (60 mg) and MeOH (10 mL), was added. After filtration the yellow solid was chromatographed using EtOAc/hexane (2:3 to 1:2) as eluent. The yellow powdery [Cp(PPh$_3$)$_2$Ru(C≡CC$_6$H$_4$)]$_3$C(OMe) was isolated in 30% yield (0.36 g). Anal. Calcd for $C_{148}H_{118}OP_6Ru_3$: C 74.02, H 4.95. Found: C 73.70, H 5.01. $^1$H NMR (300 Mhz, CDCl$_3$, 25° C., TMS) : 3.08 (s, 3 H, OCH$_3$), 4.29 (s, 15 H, Cp), 7.04–7.09, 7.15–7.21, 7.45–7.49 (m, 102 H, PPh$_3$ and C$_6$H$_4$). $^{13}$C NMR (100 MHz, CDCl$_3$, 25° C., TMS): $\delta$=52.0 (OCH$_3$), 85.2 (Cp). 87.2 (C(C$_6$H$_4$)$_3$), 114.5 (Ru—C≡C$_\beta$, 115.0 (t, J$_{c-p}$=24.8 Hz, RU—C$_\alpha$≡C), 127.2 (t, J$_{c-p}$=4.4 Hz, C$_{meta}$ of PPh$_3$). 128.6 (C$_{para}$ of PPh$_3$), 128.6 (C$_6$H$_4$), 129.6 (C$_6$H$_4$), 129.6 (C$_6$H$_4$), 133.9 (t, J$_{c-p}$=4.9 Hz, C$_{ortho}$ of PPh$_3$), 139.0 (t, J$_{c-p}$=20.8 Hz, C$_{ipso}$ of PPh$_3$), 139.2 (C$_6$H$_4$); $^{31}$P NMR (120 MHz, CDCl$_3$, 25° C., 85% H$_3$PO$_4$): $\delta$=51.0; IR (KBr, cm$^{-1}$): 1089 (m, s, C—O) 2072 (vs C≡C). A solution of HBF (0.2 mL, 54% Et$_2$O solution) was slowly added to a THF (5 mL) solution of [Cp(PPh$_3$)$_2$Ru(C≡CC$_6$H$_4$)]$_3$C(OMe) (80 mg, 0.033 mmol) that was prechilled to 0° C. The resulting mixture was stirred for 5 minutes, and 0.5 mL of Et$_3$N was added. The volume of the solution was reduced to 2 mL, and 25 mL of Et$_2$O was added. The solution was filtered and the solid was washed with H$_2$O and Et$_2$O. The crude product was recrystallized from CH$_2$Cl$_2$/hexane to afford green powdery [{CP(PPh$_3$)$_2$Ru(C≡CC$_6$H$_4$)}$_3$C] [BF$_4$].2CH$_2$Cl$_2$ in 80% yield (82 mg) The final product is relatively air sensitive. Anal. Calcd for $C_{150}H_{121}BCl_4F_4P_6Ru_3$: C 68.21, H 4.62. Found: C 68.17, H 4.83. T$_{decomp}$=197° C. $^1$H NMR (300 MHz, CDCl$_3$, 25° C., TMS): 4.47 (s, 15 H, Cp), 5.27 (s, 4 H, CH$_2$Cl$_2$), 7.10–7.16, 7.25–7.28, 7.36–7.44 (m, 102 H, Ph and C$_6$H$_4$). $^{13}$C NMR (100 MHz, CDCl$_3$, 25° C., TMS) : $\delta$=87.0 (Cp), 127.6 (J$_{c-p}$=4.7 Hz, C$_{meta}$ of PPh$_3$), 128.4 (Ru—C≡C$_\beta$), 128.9 (C$_{para}$ of PPh$_3$), 131.6 (C$_6$H$_4$), 133.7 (t, J$_{c-p}$=5.1 Hz, C$_{ortho}$ of PPh$_3$), 135.4 (C$_6$H$_4$), 136.9 (C$_6$H$_4$), 137.6 (t, J$_{c-p}$=21.6 Hz, C$_{ipso}$ of PPh$_3$), 139.9 (C$_6$H$_4$), 166.2 (t, J$_{c-p}$=23.5 Hz, Ru—C≡C), 174.2 (C(C$_6$H$_4$)$_3$); $^{31}$P NMR (120 MHz, CDCl$_3$, 25° C., 85% H$_3$PO$_4$): $\delta$=50.8; IR (KBr, cm$^{-1}$): 1090 (m, BF$_4$), 1986 (vs, C≡C): VIS/NIR (CH$_2$Cl$_2$) $\lambda_{max}$(nm), $\epsilon$(10$^4$M$^{-1}$cm$^{-1}$): 974 nm, $\epsilon$=11.5, f=1.34.

EXAMPLE 7

Resonance and near-IR absorbing property demonstrated by organometallic compounds of this invention The novel organometallic compounds exist as conjugated systems which can be seen from the spectroscopic data described in the above examples. For example, the methylene protons (d=3.60 ppm in CD$_3$CN) of NEt$_2$ in [Cp (PPh$_3$)$_2$Ru(C≡C—C$_6$H$_4$C (C$_6$H$_4$NEt$_2$—p$_2$)] [BF$_4$] (see Example 1, supra), or the methyl protons (d=3.29 ppm in CD$_3$CN) of NMe$_2$ in [((Cp) Ru (PPh$_3$)$_2$($\alpha$—C≡C)—C$_6$H$_4$)$_2$ —C$^+$—(C$_6$H$_4$—NMe$_2$—p)] [BF$_4$$^-$] (see Example 2, supra) exhibit chemical shifts at much lower field than those of their alcohol precursors in which no resonance from amino group is possible (NEt$_2$, 3.31 ppm; NMe$_2$, 2.90 ppm in CD$_3$CN). Further, the chemical shifts of the methylene protons of NEt$_2$ in [Cp(PPh$_3$)$_2$Ru(C≡C—C$_6$H$_4$C (C$_6$H$_4$NEt$_2$—p$_2$)] [BF$_4$] are similar to those of ethyl violet (d=3.56 ppm in CD$_3$CN) and at lower field than those of the methylene protons of N,N-diethylaniline (d=3.35 ppm in CD$_3$CN). Evidence that the metal complex moiety contributes significantly to the conjugated system of the organometallic compounds include: (1) the chemical shifts of the $\alpha$-carbons in ([Cp(PPh$_3$)$_2$Ru(C≡C—C$_6$H$_4$C(C$_6$H$_4$NEt$_2$—p$_2$)] [BF$_4$], d=146.0 ppm; [((Cp)Ru(PPh$_3$)$_2$($\alpha$—C≡C)—C$_6$H$_4$)$_2$—C$^+$—(C$_6$H$_4$—NMe$_2$-p)] [BF$_4$$^-$], d=158.7 ppm) in the ruthenium s-acetylide moiety appear at significantly lower fields than those of typical ruthenium s-acetylide; (2) the C≡C stretching frequencies of [Cp(PPh$_3$)$_2$Ru(C≡C—

C₆H₄C(C₆H₄NEt₂-p₂)] [BF₄] (2017 cm⁻¹) and [((Cp)Ru(PPh₃)₂(α—C≡C)—C₆H₄)₂—C⁺—(C₆H₄—NMe₂-p)] [BF₄⁻] (2035 sh, 1995 vs cm⁻¹) occur in the low energy region among ruthenium s-acetylides; (3) the considerable bathochromic shift of the electronic absorption spectra of [Cp(PPh₃)₂Ru(C≡C—C₆H₄C(C₆H₄NEt₂-p₂)] [BF₄] ($\lambda_{max}$=725 nm in CH₂Cl₂; 715 nm in CH₃CN), and [((η⁵—C⁵H⁵)Ru(PPh₃)₂(α—C≡C)—C₆H₄)₂—C⁺—(C₆H₄—NMe₂-p)] [BF₄⁻] ($\lambda_{max}$=855 nm in CH₂Cl₂; 850 nm in CH₃CN) with those of ethyl violet ($\lambda_{max}$=587 nm in CH₂Cl₂) and azulene analogs of the triphenyl cation, di(1-azulenyl)[4-(dimethylamino)phenyl]methyl cation ($\lambda_{max}$=615 nm in CH₃CN) and (1-azulenyl)bis[4-(dimethylamino)phenyl]methyl cation ($\lambda_{max}$=608 nm in CH₃CN). Absorbance of even longer wavelength (974 nm) can be observed when each of the three aromatic moieties contain a metal complex (see Example 6, supra).

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound consisting of three heteroaromatic moieties respectively bonded to a methyl carbocation, and a counterion; wherein each of the three aromatic moieties is optionally substituted with an electron-donating group, at least one of the three aromatic moieties is bonded to a metal complex moiety, either directly or through a linker, and the methyl carbocation, the aromatic moieties, the metal complex moiety, and the linker form a conjugated system.

2. The compound of claim 1, wherein the heteroaromatic moiety is pyridinyl, furanyl, thienyl, or pyrrolyl.

3. The compound of claim 2, wherein the heteroaromatic moiety is or thienyl.

4. The compound of claim 1, wherein the metal complex moiety is a Ru, Fe, Ni, or Pt metal complex.

5. The compound of claim 4, wherein the metal complex moiety is a Ru or Fe metal complex.

6. The compound of claim 5, wherein the Ru metal complex moiety is [(Cp)Ru(PPh₃)₂(α—C≡C—)] and the Fe metal complex moiety is [(Cp)Fe(Cp—)].

7. The compound of claim 5, wherein the heteroaromatic moiety is pyridinyl, furanyl, thienyl, or pyrrolyl.

8. The compound of claim 6, wherein the heteroaromatic moiety is or thienyl.

9. The compound of claim 1, said compound having the following formula:

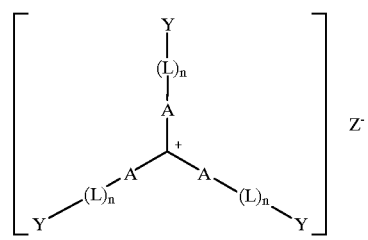

wherein each A, independently, is a heteroaromatic fused ring or

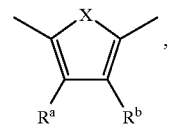

in which X is —O—, —S—, —NH—, or —N(alkyl)—, and each of $R^a$ and $R^b$, independently, is H, alkyl, alkoxy, or $NR^1R^2$ with each of $R^1$ and $R^2$, independently, being H or alkyl;

each L is an electronically conjugated linker moiety;

each n, independently, is 0, 1, 2, or 3;

each Y, independently, is H, alkoxy, $NR^3R^4$, or a Ru, Fe, Ni, or Pt metal complex, wherein $R^3$ and $R^4$, independently, is H, alkyl, cycloalkyl, heterocycloalkyl, aryl, or heteroaryl; and Z is a counterion.

10. The compound of claim 9, wherein each A, independently, is

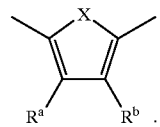

11. The compound of claim 10, wherein X is —S—.

12. The compound of claim 11, wherein each L, independently, is —CH═CH—B—; B is an aromatic fused ring or

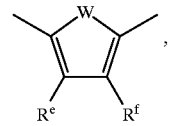

in which W is —O—, —S—, —NH—, —N(alkyl)—, or —C($R^g$)═C($R^h$)—; and each of $R^e$, $R^f$, $R^g$, and $R^h$, independently, is H, alkyl, alkoxy, or $NR^5R^6$ with $R^5$ and $R^6$, independently, being H or alkyl.

13. The compound of claim 12, wherein B is

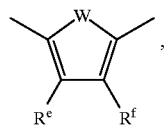

in which W is —S— or —CH=CH—, and n is 0 or 1.

14. The compound of claim 13, wherein one of the Y moieties is a Ru metal complex, and each of the remaining Y moieties, independently, is $NR^1R^2$ with each of $R^1$ and $R^2$, independently, being alkyl.

15. The compound of claim 13, wherein one of the Y moieties is $NR^3R^4$ with each of $R^3$ and $R^4$, independently, being alkyl, and each of the remaining Y moieties, independently, is a Ru metal complex.

16. The compound of claim 13, wherein each of the Y moieties, independently, is a Ru metal complex.

17. The compound of claim 9, wherein each Y, independently, is $NR^3R^4$, a Ru metal complex, or a Fe metal complex.

18. The compound of claim 17, wherein one of the Y moieties is a Ru metal complex, and each of the remaining Y moieties, independently, is $NR^3R^4$ with each of $R^3$ and $R^4$, independently, being alkyl.

19. The compound of claim 17, wherein one of the Y moieties is $NR^3R^4$ with each of $R^3$ and $R^4$, independently, being alkyl, and each of the remaining Y moieties, independently, is a Ru metal complex.

20. The compound of claim 17, wherein each of the Y moieties, independently, is a Ru metal complex.

21. The compound of claim 17, wherein each A, independently, is

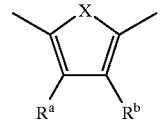

in which X is —S—.

22. The compound of claim 21, wherein n is 0 or 1; each L, independently, is —CH=CH—B—; and B is an aromatic fused ring or

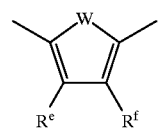

in which W is —O—, —S—, —NH—, —N(alkyl)—, or —C($R^g$)=C($R^h$)—, each of $R^e$, $R^f$, $R^g$, and $R^h$, independently, being H, alkyl, alkoxy, or $NR^5R^6$, wherein $R^5$ and $R^6$, independently, is H or alkyl.

* * * * *